(12) United States Patent
Coleman et al.

(10) Patent No.: US 9,321,052 B2
(45) Date of Patent: Apr. 26, 2016

(54) FLUID SAMPLING FLASK HAVING CAP AND VALVE ASSEMBLY

(71) Applicant: Weatherford/Lamb, Inc., Houston, TX (US)

(72) Inventors: Todd M. Coleman, Fairmont, IL (US); Gavin A. Steele, White Head, IL (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 14/279,661

(22) Filed: May 16, 2014

(65) Prior Publication Data

US 2014/0338289 A1    Nov. 20, 2014

Related U.S. Application Data

(60) Provisional application No. 61/824,778, filed on May 17, 2013.

(51) Int. Cl.

| | | |
|---|---|---|
| B65B 1/04 | (2006.01) | |
| B01L 3/00 | (2006.01) | |
| G01N 1/10 | (2006.01) | |
| G01N 33/18 | (2006.01) | |
| B65B 55/02 | (2006.01) | |
| G01N 1/20 | (2006.01) | |

(52) U.S. Cl.
CPC . *B01L 3/505* (2013.01); *G01N 1/10* (2013.01); *G01N 33/18* (2013.01); *B01L 2200/026* (2013.01); *B01L 2300/049* (2013.01); *B01L 2300/0809* (2013.01); *B65B 55/022* (2013.01); *G01N 2001/2071* (2013.01)

(58) Field of Classification Search
None
See application file for complete search history.

(56) References Cited

U.S. PATENT DOCUMENTS

| | | | | |
|---|---|---|---|---|
| 2,374,135 | A | * | 4/1945 | Roper .................... G01V 9/007 202/205 |
| 5,603,436 | A | * | 2/1997 | Leoncavallo et al. ......... 222/525 |

FOREIGN PATENT DOCUMENTS

WO    WO 2010141094 A2 * 12/2010    ......... B65D 31/145

OTHER PUBLICATIONS

Coghlan, Coghlan's Emergency Drinking Water Germicidal Tablet EPA Reg. No. 79533-1, Jan 12, 2005, Coghlan, p. 1-2 including date stamps.*
Hackley et al, Collection and Analysis of Gas Samples from Groundwater, 2012, Isotech, Stray Gas Conference 2012, 27 pages.*
Texas Technologies, "5 MIL Nylon/Poly Biax Product Data Sheet," obtained from www.TexasTechnologies.com, 1 page.
"Film Data Sheet NP500X," obtained from www.standuppouches.net, 1 page.

(Continued)

*Primary Examiner* — Binh X Tran
*Assistant Examiner* — David Cathey, Jr.
(74) *Attorney, Agent, or Firm* — Blank Rome, LLP

(57) ABSTRACT

A container for collecting water samples to determine dissolved gas includes a flask-type pouch with a spout. A removable cap and valve install on the spout. The valve includes an adapter that fits with an O-ring or other seal inside the mouth of the spout. The valve includes a valve element, which can be a one-way, self-closing type of valve, that fits with an O-ring or other seal inside the end of the adapter. A cap of the container fits over the adapter and affixes to the spout to hold the valve on the spout. In use, the cap can be removed so that the valve element and adapter can be removed for filling the pouch. Otherwise, the cap can remain in place so filling can be performed through the valve element. A tamper-evident ring on the cap may be provided to ensure the integrity of the sample contained in the flask.

12 Claims, 7 Drawing Sheets

(56) References Cited

OTHER PUBLICATIONS

"Film Data Sheet NP500," obtained from www.standuppouches.net, 1 page.

Isotech Laboratories Inc., "Collection of Ground Water Samples from Domestic and Municipal Water Wells for Dissolved Gas Analysis," regarding DG Bottle, obtained from www.isotechlabs.com, 1 page.

Isotech Laboratories Inc., "Collection of Ground Water Samples from Domestic and Municipal Water Wells for Dissolved Gas Analysis," regarding IsoBag, obtained from www.isotechlabs.com, 1 page.

Isotech Laboratories Inc., "High-Precision Isotopic Analysis: Sampling Products > Other > Dissolved Gas Containers," obtained from www.isotechlabs.com, (c) 2012, 1 page.

Halkey-Roberts, "Luer Lock Valve," dated Sep. 20, 1994, Customer Drawing No. C2470100XX, Rev. G, 1 page.

Halkey-Roberts, "Luer Lock Valve," dated Dec. 17, 2009, Customer Drawing No. C247021001, Rev. B, 1 page.

Isotech Laboratories Inc., "Collecting Wellhead Samples in Single-Use IsoTubes," obtained from www.isotechlabs.com, 1 page.

\* cited by examiner

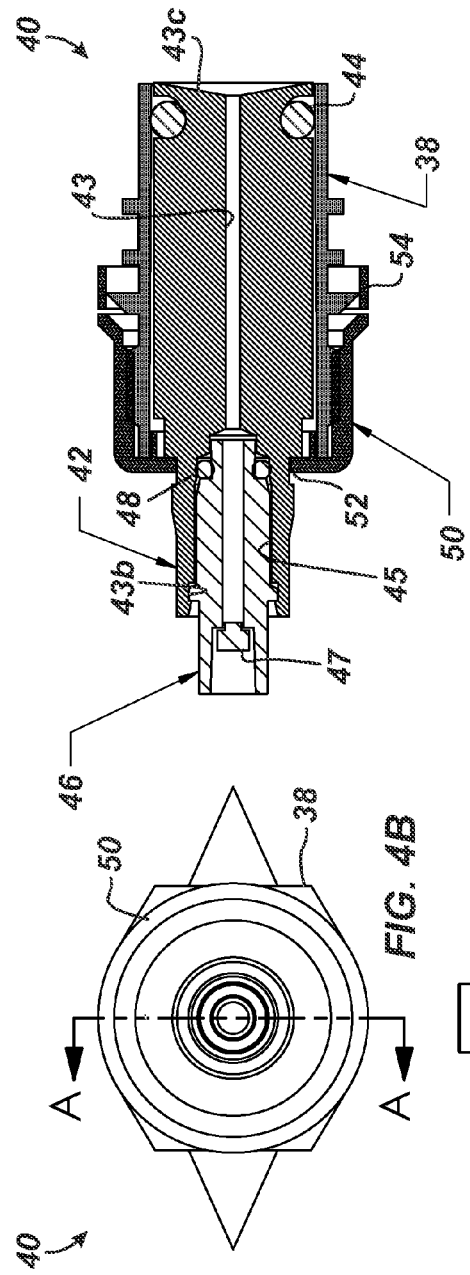
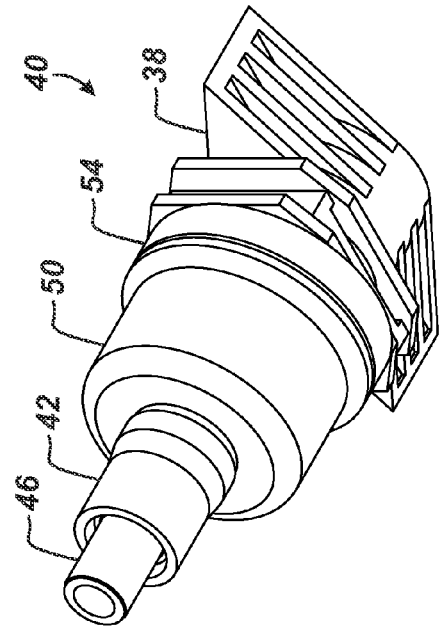
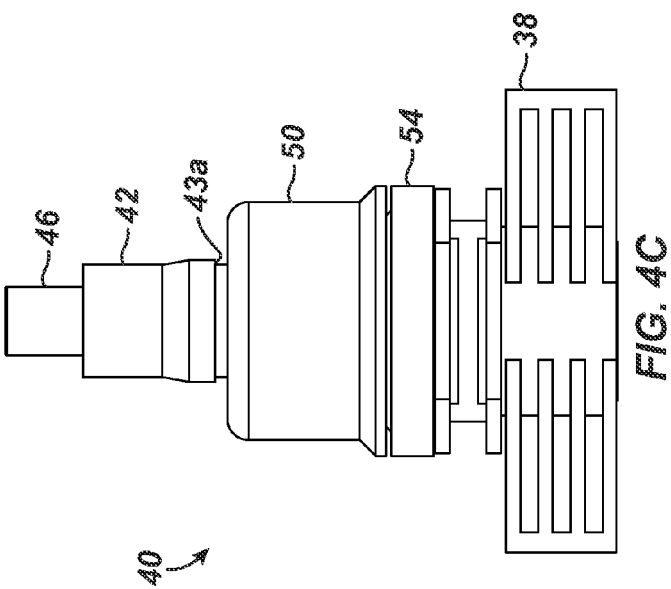
FIG. 4A
FIG. 4B
FIG. 4C
FIG. 4D

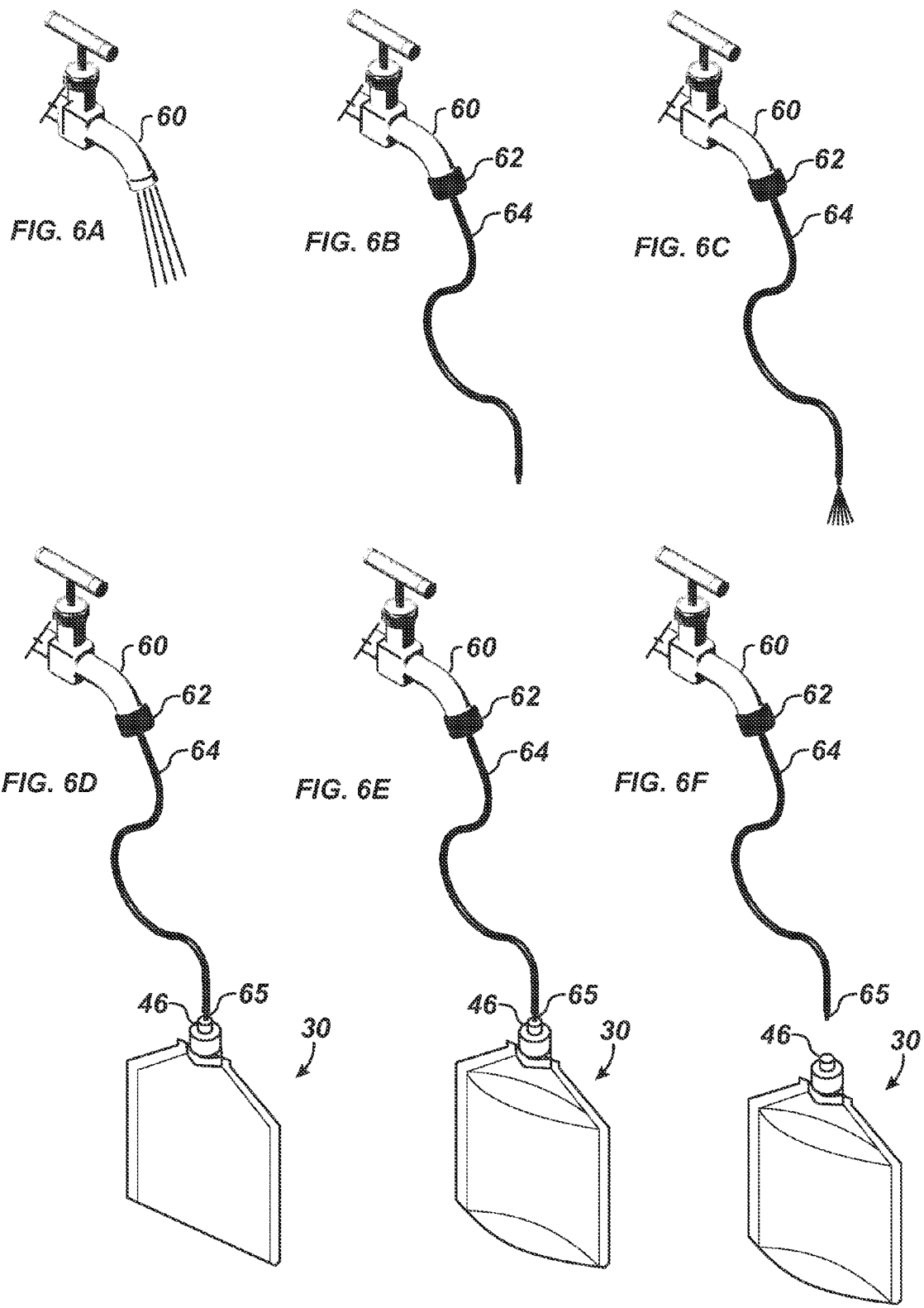

FLUID SAMPLING FLASK HAVING CAP AND VALVE ASSEMBLY

CROSS-REFERENCE TO RELATED APPLICATIONS

This application claims the benefit of U.S. Provisional Appl. 61/824,778, filed May 17, 2013, which is incorporated herein by reference in its entirety.

BACKGROUND OF THE DISCLOSURE

Dissolved gas sampling and analysis has been increasing in regularity so potential effects of fracturing activity in wells can be monitored. Traditionally, bags and plastic bottles are used to collect water for determining dissolved gas, such as methane, ethane, and propane, in the water samples. The type of container used can depend on the type of data needed from a sample. Both containers (bags and bottles) generally provide a sufficient sample for chemical and isotopic analysis of dissolved gas for identifying the source of the gas. If the amount of gas in the water is to be quantified to ppm or cc/L, the type of container needed may depend on the amount of gas present.

A dissolved gas bottle can be used to quantify the amount of gas in the water if the gas content is below saturation at atmospheric pressure (i.e., does not form bubbles). A bag is preferred when the amount of gas in the water is above the saturation limit because both the dissolved gas and the free gas are quantitatively collected.

A dissolved gas bottle is designed to collect samples from domestic water wells, and the bottle can hold about 1-liter, which makes it large enough for compositional and isotopic analysis of the dissolved gas. The bottle has a cap-mounted septum so it is not necessary to open the bottle during analysis, which reduces the potential for contamination of the sample. Each bottle also contains a bactericide capsule to prevent degradation of the gas.

FIG. 1 illustrates a sample bag 10 according to the prior art. This bag 10 resembles the IsoBags® available from Isotech Laboratories, Inc. of Champaign, Ill. (ISO BAG is a registered trademark of Isotech Laboratories, Inc.) The bag 10 consists of a film pouch 12, which can come with a bactericide capsule 14 inside to prevent degradation of the sample. A spout 20 is permanently affixed inside a side hole in the pouch 12 using retaining rings, gaskets, or other permanent fixtures. The spout 20 also includes a self-closing type of valve 22, such as a luer valve used for medical purposes and available from Qosina Corp. of New York.

Although the existing bottles and bags are suitable for taking domestic water samples to determine dissolved gas, sampling technicians are continually striving for a more versatile sampling container that can be readily used in the field and handled in the lab.

The subject matter of the present disclosure is directed to overcoming, or at least reducing the effects of, one or more of the problems set forth above.

BRIEF DESCRIPTION OF THE DRAWINGS

FIGS. 4A-4D illustrate cross-section, top, side, and perspective views of the cap and valve assembly of the disclosed flask.
FIGS. 6A-6F illustrates steps for sampling a water source with the disclosed flask.

SUMMARY OF THE DISCLOSURE

Figure 1:
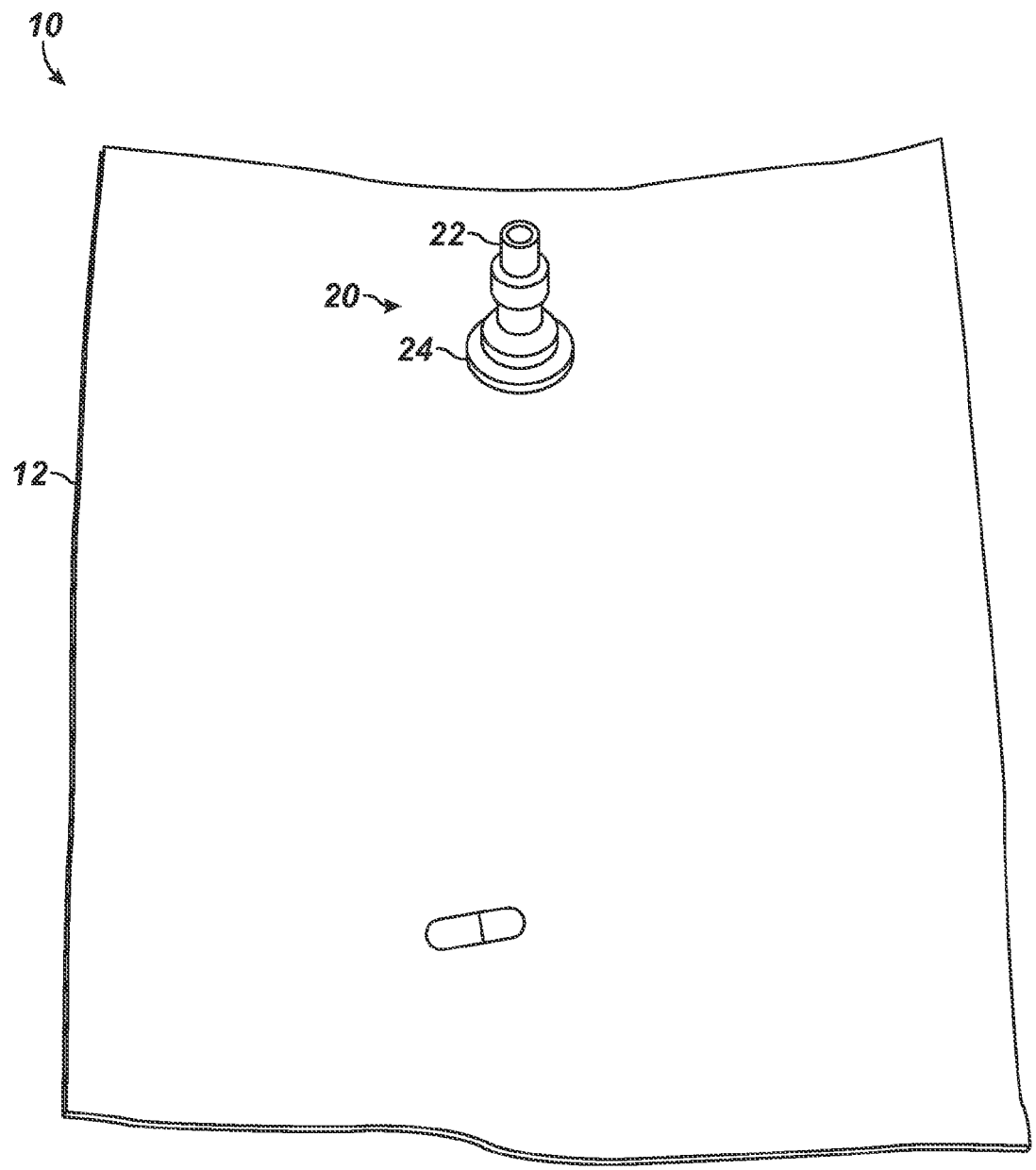
FIG. 1 illustrates a sample bag according to the prior art.

A flask can be used to obtain, from a source, a liquid sample having dissolved hydrocarbon gas. The flask has a pouch, a spout, a removable valve, and a removable cap and may also have a bactericide capsule. The pouch is composed of a flexible material and is evacuated. The flexible material of the pouch is selected to mitigate permeability and interaction with the hydrocarbon gas.

The spout is sealably affixed to an opening of the pouch at a top end. The removable valve is removably disposed in the spout and is operable to communicate the liquid sample with the dissolved hydrocarbon gas into the pouch. The removable cap is removably disposed on the spout and retains at least a portion of the removable valve in the spout.

The pouch can have first and second sidewalls affixed along longitudinal edges and can have a bottom piece affixed to the first and second sidewalls at a bottom end of the pouch. When the pouch is filled with the liquid sample, the first and second sidewalls and the bottom piece expand outward to form a base on which the flask is supportable.

The removable cap can have a tab removably affixing the cap to the spout. The removable valve can have first and second members. The member reduces dead volume between the spout and the pouch, and the second member controls the flow of the liquid sample into the pouch. In particular, the first member can be disposed in the spout and can be held therein with the cap. The first member can have an external seal sealing with the spout and has a fluid passage defined therethrough. The second member can be disposed at least partially in the fluid passage of the first member and can an external seal sealing with the fluid passage. To control flow of the liquid sample, the second member has a self-closing valve element.

The spout is usable to fill the pouch with the liquid sample when the removable cap and the removable valve are selectively removed from the spout. In other modifications, a capsule containing a bactericide can be disposed in the pouch. Additionally, a filing tube can be affixed to the removable valve and can have an adapter adapted to connect to the source.

To manufacture such a flask for obtaining a liquid sample from a source, a pouch composed of a flexible material is formed such that the pouch has top and bottom ends and has an opening at the top end. A spout is sealably affixed to the opening of the pouch at the top end, and a removable valve is positioned in the spout for being operable to communicate the liquid sample into the pouch. The removable valve is retained in the spout by positioning a removable cap on the spout. The pouch is evacuated to eliminate contamination of the sample when collected.

To obtain a liquid sample from a source, a removable valve on a spout of a pouch is connected to the source, and the removable valve on the spout is opened. The pouch is filled with the liquid sample passing through the removable valve and the spout. A standable base forms on the pouch as sidewalls of the pouch expand outward from one another at a bottom end of the pouch during filling. The removable valve on the spout is closed once the pouch is filled.

The foregoing summary is not intended to summarize each potential embodiment or every aspect of the present disclosure.

DETAILED DESCRIPTION OF THE DISCLOSURE

Figure 2A:
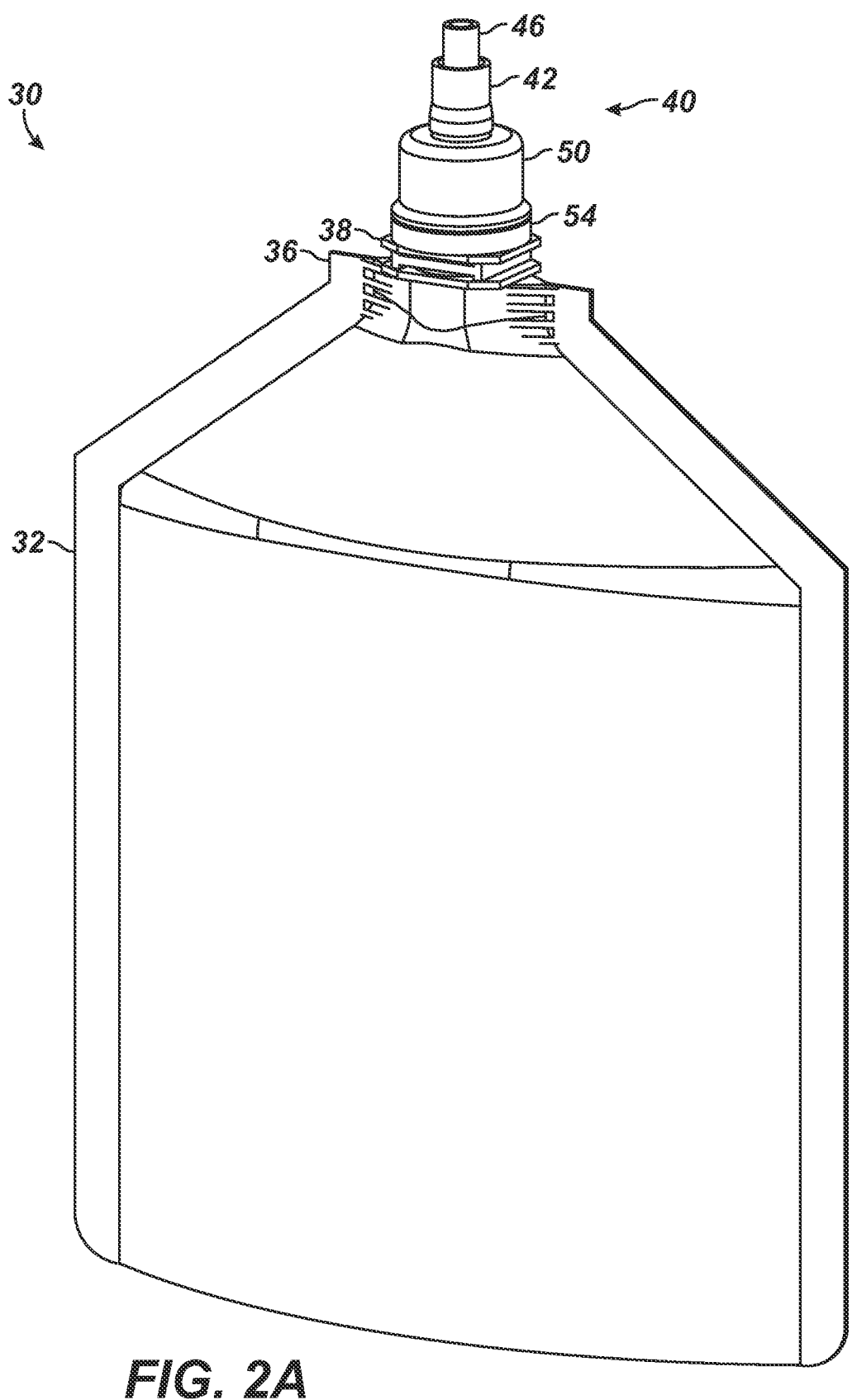
FIGS. 2A-2B show side views of a sample flask according to the present disclosure.
Figure 2B:
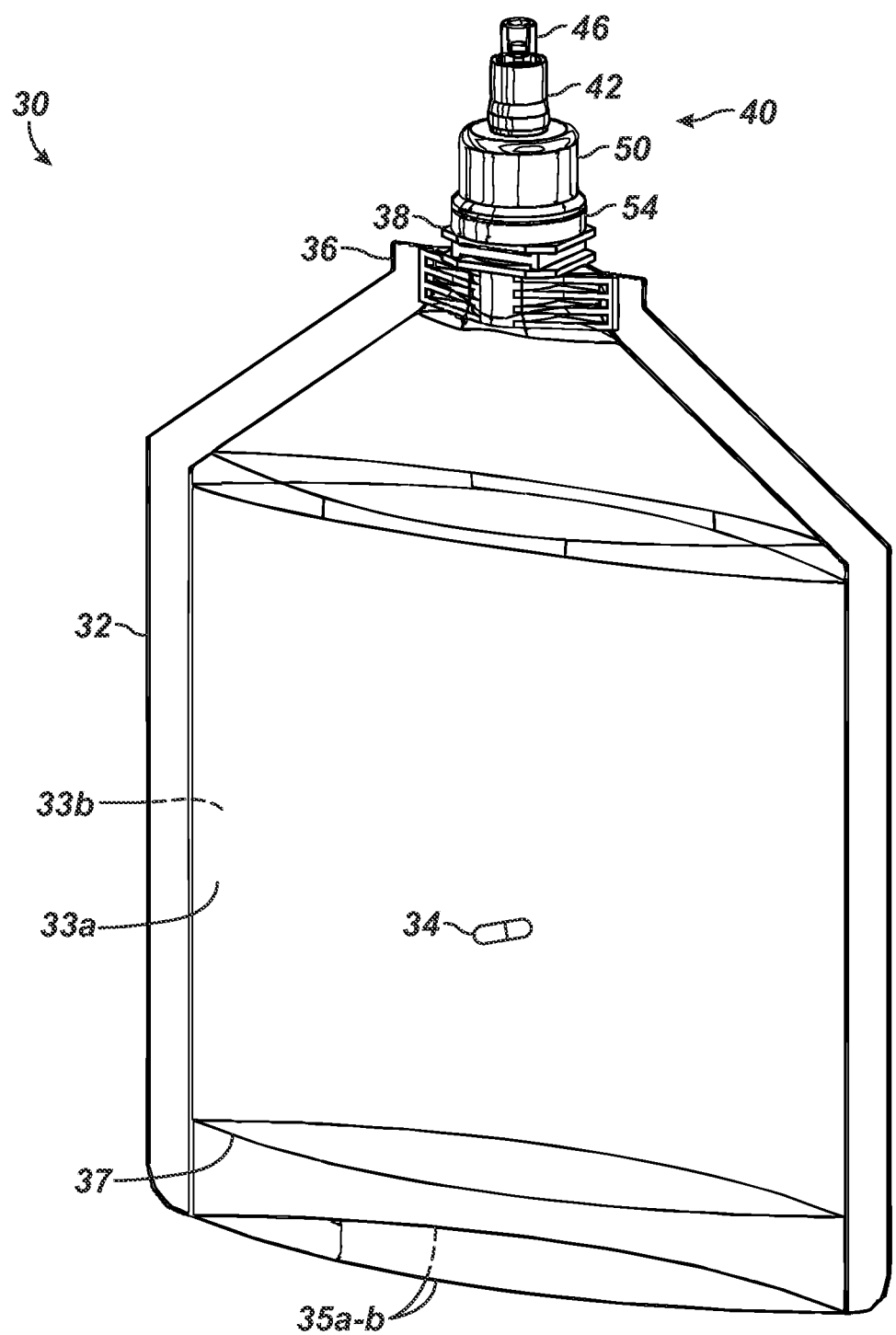

FIGS. 2A-2B show side views of a sample container 30 according to the present disclosure. The container 30 is a flask having a stand-up pouch 32 with a removable cap 50 and a removable valve 40 disposed in a spout 38. The pouch 32 can have any suitable volume, such as 750 ml, for a particular sample. The pouch 32 is shipped evacuated for later filling with the sample, and a bactericide capsule 34 can be pre-inserted in the pouch 32.

The pouch 32 is composed of a flexible material, such as a puncture-resistant plastic film with its back side colored white to assist in coloration observations of a sample. The material for the pouch 32 is preferably suited for containing the light hydrocarbon gasses of interest that may be dissolved in water samples taken near areas of well fracturing operations. The material is therefore preferably impermeable to the hydrocarbons and does not interact with them. This will help the pouch 30 retain the gases close to the initial sampled level for an extended period of time after collection (i.e., even as long as 150 days or so).

One suitable material for the pouch 32 is a BIAX Nylon/Poly laminated barrier film that can be 5 mils thick or so. One layer of the material may be 1-mil of BIAX Nylon, and another layer may be 4-mil Ethylene vinyl alcohol (EVOH)/Linear Low-Density Polyethylene (LLDPE). Other configurations could be used.

The spout 38 is affixed to a spouted end 36 of the pouch 32 using heat molding, shrink fitting, adhesion, or other suitable technique. The removable cap 50 and the removable valve 40 fit on the spout 38, and the valve 40 has a valve element 46 and an adapter 42. The cap 50 has a tamper evident ring 54. The valve element 46 can be a self-closing type of luer valve, such as available from Qosina Corp. Various attachments can be used for proper filling of the pouch 32, such as described below.

As best shown in FIG. 2B, the flask 30 is self-standing once filled. In particular, the pouch 32 of flexible material has two sides 33a-b affixed together along their longitudinal edges. For example, heat seals of the polyethylene on the sidewalls 33a-b can affix the edges together. The bottom end of the pouch 32 opposite the spouted end 36 has a bottom piece 37 affixed to the two sides 33a-b. As the pouch 32 is filled with the water sample, the two sides 33a-b expand outward from one another at the bottom of the pouch 32 and the pleated bottom piece 37 opens up to form a bottom of the flask 30, which allows the flask to hold a larger sample. In this regard, the larger the sample obtained will mitigate magnified errors of the amount of dissolved gas in the water, which would be the case if smaller samples be used. Preferably, lower edges 35a-b of the two sides 33a-b extend beyond the bottom piece 37 and form a base, which can help support the flask 30 upright.

Furthermore, the pouch 32 of the flask 30 narrows at the top toward the opening 36 to direct all collected gases toward the valve element 46 when it is standing upright. This aids in extraction and measurement of the gases during subsequent analysis. Moreover, the flask 30 can be substantially evacuated before use and can remain so over time, which can eliminate air contamination during later sample collection.

Figure 3:
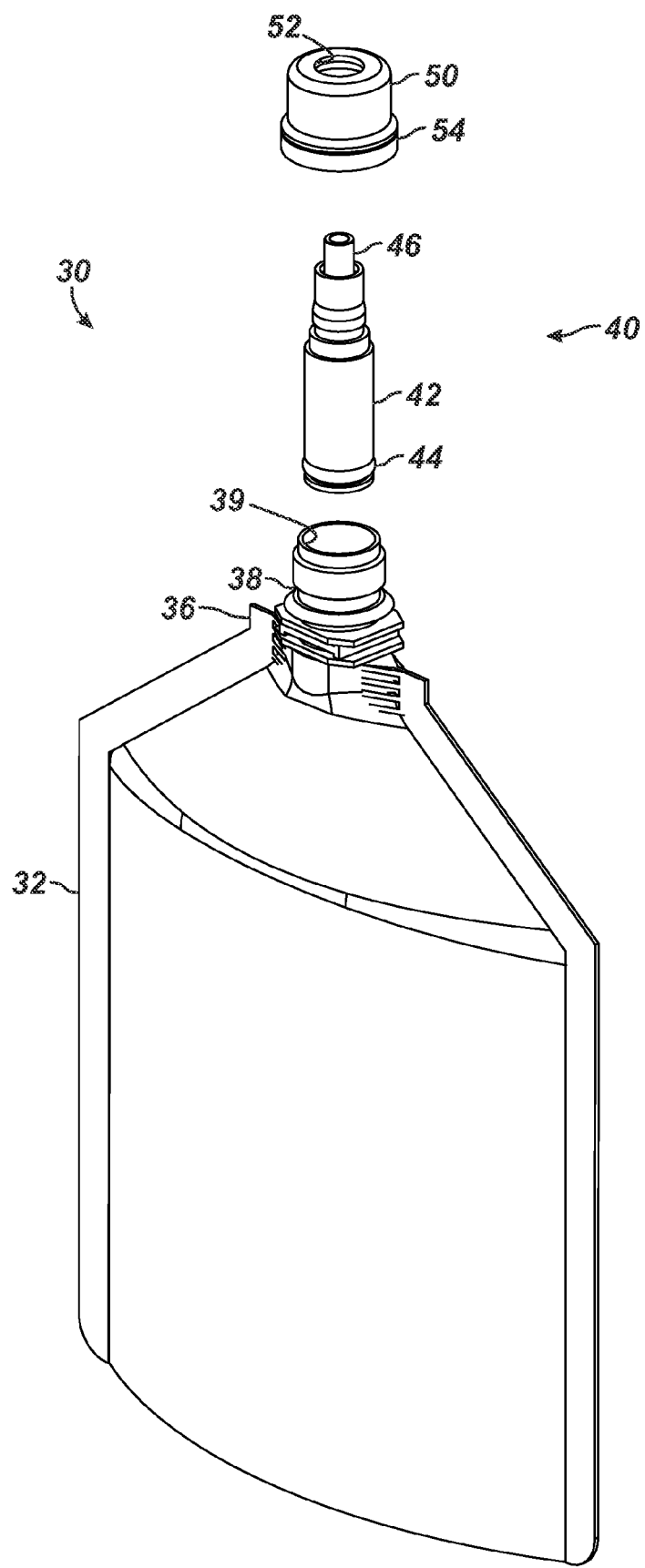
FIG. 3 illustrates the components of the disclosed flask separate from one another.

FIG. 3 illustrates the components of the disclosed flask 30 separate from one another, and FIGS. 4A-4D illustrate cross-section, top, side, and perspective views of the cap 50 and valve 40 of the disclosed flask 30. Additionally, FIG. 5 illustrates an exploded view of the components for the cap 50 and valve 40.

Figure 5:
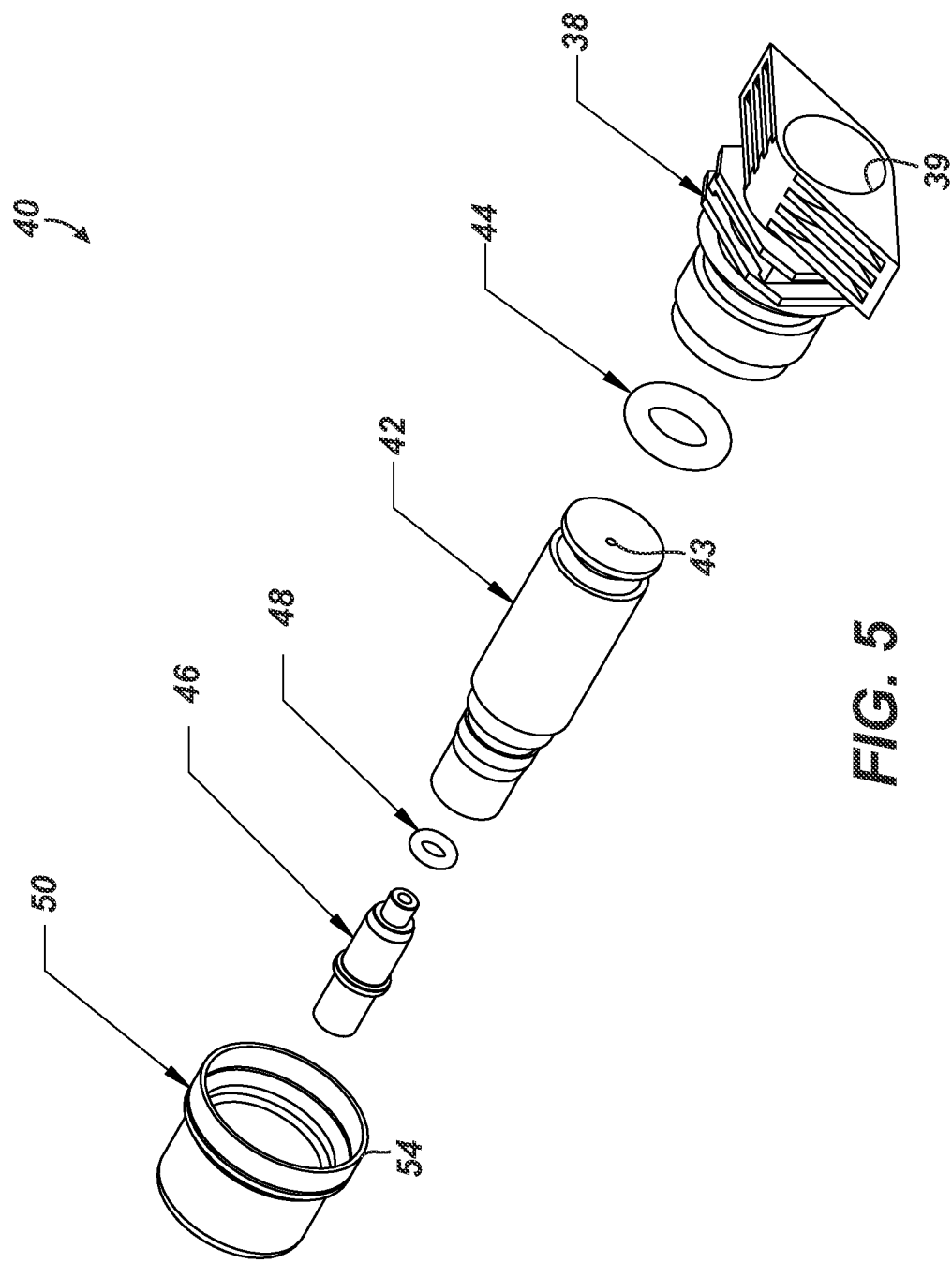
FIG. 5 illustrates an exploded view of the components for the cap and valve assembly.

As shown in these FIGS. 3 through 5, the cap 50 and valve 40 specifically includes the spout adapter 42, the valve element 46, and the cap 50. Although the adapter 42 and valve element 46 are disclosed and shown as separate components, the valve 40 for the disclosed flask 30 can be an integral component combining the features of these two elements.

The adapter 42 has an O-ring 44 disposed on one end and has a central bore 43 therethrough. Preferably, the O-ring 44 is positioned at the inner end of the mouth 39 toward the inside of the pouch 32, as best shown in FIG. 4A. The adapter 42 inserts into the cylindrical mouth 39 of the spout 38 to form a sealed fit.

Use of the spout adapter 42 with the inner positioned seal 44 can help minimize any void space in the pouch 32 beyond the inner end of the mouth 36 where measurable gas could be trapped. In particular, the lower end of the adapter 42 can extend flush to the inner end of the spout's mouth 39, reducing the amount of void space in the mouth 39. Additionally, the central bore 43 of the adapter 42 is considerably narrower than the spout 38, reducing the void space. Also, the base 43c of the adapter 42 surrounding the bore 43 is conical in shape as best shown in FIG. 4A. This conical shaped base 43c helps to direct all gases present in the flask's pouch 32 toward the top of the container for complete extraction for volume measurement of the gaseous components.

As best shown in FIG. 4A, another O-ring 48 fits on the end of the valve element 46, and the valve element 46 inserts inside an expanded opening 45 in the end of the spout adapter 42 in a sealed fit. This arrangement further reduces the amount of void space at the spout 38. The valve element 46 has a self-sealing element 47 disposed therein that can open and allow fluid flow into the valve element 46, central bore 43, and spout 38, but can prevent reverse fluid flow.

Finally, the cap 50 installs (e.g., press fits or threads) on the spout 38 to hold the spout adapter 42 in the spout 38. The adapter 42 then extends through a central opening 52 of the cap 50. The cap 50 can have a tamper-evident ring 54 that engages a shoulder of the spout 38 and tears from the cap 50 if the cap 50 is removed from the spout 38.

The flask 30 can be used in a number of sampling applications and is more versatile than existing sampling containers (e.g., bottles and bags). Primarily, the flask 30 is used for collecting water for determining dissolved gas of light hydrocarbon (e.g., methane, ethane, propane, etc.). The flask 30 helps to simplify and standardize the collection and determination of dissolved gas content in water wells.

The flask 30 is more robust than the conventional bags so samples are less likely to be lost by damage and the like. Filing of the flask 30 is simplified so there is less chance of human error or variability in sampling. The cap 50 and the valve 40 can remain affixed on the spout 38 when collecting water samples for dissolved gas as this helps ensure the integrity of the sample. In this regards, the tamper-evident ring 54 helps to identify and flag potential variability in sampling protocol.

Finally, the removable cap 50 and the valve 40 allow the flask 30 to be used for other sampling applications. For example, having the cap 50 and valve 40 be removable from the spout 38 allows the bactericide capsule 34 to be removed if certain water/gas sampling applications are to be performed. The tamper-evident ring 54 will detach when this is done.

Additionally, having the large mouthed spout 38, the adapter 42, and the valve element 46 in a modular arrangement as disclosed allows the flask 30 to be used selectively for sampling as desired. For example, the cap 50 and the valve 40 can be removed from the spout 38 by removing the cap 50 and then removing the valve element 46 and the adapter 42 together from the spout 38. As noted above, all of these components 42, 46, and 50 may be removed together as a unit. With these components 42, 46, and 50 removed, the open spout 38 can allow for faster filling of the flask 30 if unsealed filling is suitable for a particular type of sampling. It may even be desirable to remove the valve element 46 by itself from the adapter 42, but keep the adapter 42 in the spout 38 in some filling scenarios.

It is preferred that the adapter 42 and the valve element 46 be removed together. In fact, the cap 50 can preferably be affixed to the adapter 42 so that the entire assembly of adapter 42, valve element 46, cap 50, and O-rings 44 and 48 can be removed as a single unit. Although preferred, this is not strictly necessary, and each component can be separately removable. In one embodiment, the valve element 46 is not intended to be removed from the adapter 42. Instead, a rib on the valve element 46 "snaps" into a grove or radial recess 43b in the adapter opening 45, which can affix the valve element 46 permanently in place in the adapter 42. A reverse arrangement could also be used.

In a similar fashion, the cap 50 snaps over a ridge 43a on the adapter 42 that also holds the cap 50 onto the adapter 42 so that the cap 50 is semi-permanently held in place. For example, the hole 52 in the cap 50 can be slightly undersized relative to the adapter 42 so the cap 50 can be held in place when it reaches the ridge 43a. With force the cap 50 can be separated from the adapter 42, but typically the entire assembly (42, 46, 50) would remain intact as a single unit and would be removed all together from the spout 38.

As can be seen, the pouch 32 has its spouted opening 36 that defines a slit-shaped opening at the top of the pouch 32 because the pouch 32 is made from adjacent sidewalls 33a-b affixed together. Because the adapter 42 sealably fits in the spout 38 and can be removed therefrom if desired, the spout's opening 39 is preferably cylindrical for better fitting and sealing. For example, the cylindrical opening 39 allows the sealing from the O-ring 44 to situate deep inside the spout's opening 39 to reduce the amount of void volume in the flask 30. Having the spout's opening 39 be cylindrical means that the spout 38 adapts the slit-shaped open end 36 of the pouch 32 to the preferred cylindrical shaped opening 39 for fitting and sealing with the valve 40.

FIGS. 6A-6F illustrates steps for sampling a domestic water well with the disclosed flask 30. The sampling protocol for the domestic water well involves initially purging the water line 60, as shown in FIG. 6A. Then, as shown in FIG. 6B, a fill tube 64 is attached to the water line 60 with an adapter 62, and the tube 64 is then purged, as shown in FIG. 6C. At this point, the technician attaches the end fitting 65 of the tube 64 to the evacuated flask 30, as shown in FIG. 6D. The end fitting 65 is a male luer fitting that sealably mates to the flask's valve element 46, which is a female luer valve. When this end fitting 65 is inserted into the valve element 46 (for filling), it simultaneously makes a seal to the valve element 46 and also depresses the actuator pin or self-sealing element 47 in the valve element 46, which opens it. If sampling for dissolved gas, the cap 50 and valve 40 are preferably kept on the spout 38, as noted above. The technician then fills the flask's pouch 32 to about ⅔ full, as shown in FIG. 6E. Finally, the flask 30 is detached from the fill tube 64 so the filled flask 30 can be transported and stored for later analysis, as shown in FIG. 6F.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A flask for obtaining, from a source, a liquid sample having dissolved hydrocarbon gas, the flask comprising:
   a pouch composed of a flexible material and being evacuated, the pouch having top and bottom ends and having an opening at the top end;
   a spout sealably affixed to the opening of the pouch at the top end and defining a first fluid passage communicating with the pouch, the first fluid passage having a first inside dimension and defining a dead volume from a distal end of the spout to a proximal end of the spout toward the pouch;
   a removable valve removably disposed in the first fluid passage of the spout at least to the proximal end, the removable valve defining a second fluid passage with a second inside dimension less than the first inside dimension, the removable valve with the second fluid passage reducing the dead volume between the spout and the pouch and being operable to communicate the liquid sample with the dissolved hydrocarbon gas into the pouch through the second fluid passage; and
   a removable cap removably disposed on the spout and retaining at least a portion of the removable valve in the spout.

2. The flask of claim 1, wherein the pouch comprises:
   first and second sidewalls affixed along longitudinal edges; and
   a bottom piece affixed to the first and second sidewalls at the bottom end of the pouch,
   wherein the first and second sidewalls and the bottom piece expand outward during filling of the pouch with the liquid sample and form a base on which the flask is supportable.

3. The flask of claim 1, wherein the removable cap comprises a tab removably affixing the cap to the spout.

4. The flask of claim 1, wherein the removable valve comprises a first member disposed at least partially in the spout and held therein with the cap, the first member having a first external seal sealing with the spout and having a portion of the second fluid passage defined therethrough.

5. The flask of claim 4, wherein the second fluid passage at the proximal end of the first member disposed in the spout defines a conical shape.

6. The flask of claim 4, wherein the removable valve comprises a second member disposed at least partially in the portion of the second fluid passage of the first member and having a second external seal sealing with the portion of the second fluid passage, the second member having a self-closing valve element.

7. The flask of claim 6, wherein the second member is affixed in the portion of the second fluid passage of the first member.

8. The flask of claim 1, wherein the removable cap and the removable valve are removable together from the spout.

9. The flask of claim 1, further comprising a capsule containing a bactericide and disposed in the pouch.

10. The flask of claim 1, further comprising a filling tube affixable to the removable valve and adapted to connect to the source.

11. The flask of claim 1, wherein the spout is usable to fill the pouch with the liquid sample when the removable cap and the removable valve are selectively removed from the spout.

12. The flask of claim 1, wherein the flexible material of the pouch is selected to mitigate permeability and chemical interaction with the hydrocarbon gas.

\* \* \* \* \*